(12) United States Patent
Schultz

(10) Patent No.: US 10,966,832 B2
(45) Date of Patent: Apr. 6, 2021

(54) COMPLIANT BIOLOGICAL SCAFFOLD

(71) Applicant: Brent Schultz, Scottsdale, AZ (US)

(72) Inventor: Brent Schultz, Scottsdale, AZ (US)

( * ) Notice: Subject to any disclaimer, the term of this patent is extended or adjusted under 35 U.S.C. 154(b) by 0 days.

(21) Appl. No.: 17/021,802

(22) Filed: Sep. 15, 2020

(65) Prior Publication Data

US 2020/0405489 A1 Dec. 31, 2020

Related U.S. Application Data

(63) Continuation-in-part of application No. PCT/US2020/013729, filed on Jan. 15, 2020.

(60) Provisional application No. 62/792,867, filed on Jan. 15, 2019.

(51) Int. Cl.

| | |
|---|---|
| *A61F 2/28* | (2006.01) |
| *B33Y 80/00* | (2015.01) |
| *A61F 2/12* | (2006.01) |
| *A61L 15/58* | (2006.01) |
| *A61L 27/56* | (2006.01) |
| *A61L 31/06* | (2006.01) |
| *B29C 55/26* | (2006.01) |
| *A61F 2/30* | (2006.01) |

(52) U.S. Cl.
CPC .............. *A61F 2/2846* (2013.01); *A61F 2/12* (2013.01); *A61L 15/58* (2013.01); *A61L 27/56* (2013.01); *A61L 31/06* (2013.01); *B29C 55/26* (2013.01); *B33Y 80/00* (2014.12); *A61F 2002/285* (2013.01); *A61F 2002/30172* (2013.01); *A61F 2002/30181* (2013.01)

(58) Field of Classification Search
CPC .... A61F 2/28; A61F 2/2846; A61F 2002/285; A61L 27/56
See application file for complete search history.

(56) References Cited

U.S. PATENT DOCUMENTS

| | | |
|---|---|---|
| 8,049,059 B2 | 11/2011 | Bleyer et al. |
| 2013/0021151 A1 | 1/2013 | Buchkremer |
| 2015/0016563 A1 | 7/2015 | Woodroof |
| 2015/0020234 A1 | 7/2015 | Woodroof |

*Primary Examiner* — Jason-Dennis N Stewart
(74) *Attorney, Agent, or Firm* — Invention To Patent Services; Alex Hobson

(57) ABSTRACT

A compliant biological scaffold incorporates a plurality of elongated apertures that form a geometric pattern enabling biaxial expansion or contraction. An elongated aperture has a pair of nodes located on opposing sides of the aperture and between a pair of antinodes located on the extended and opposing ends of the elongated aperture. A geometric pattern may have various geometric shapes, or tiles, between the plurality of apertures. The geometric tiles have a bounded perimeter formed by the plurality of elongated apertures. A substantial portion of the elongated apertures may be configured with the antinodes proximal to one of said pair of nodes of a separate elongated aperture; wherein the antinodes are closer to one of the pair of nodes than to any other antinode. This unique arrangement of the elongated apertures may be formed in biological material in vivo or ex vivo.

39 Claims, 12 Drawing Sheets

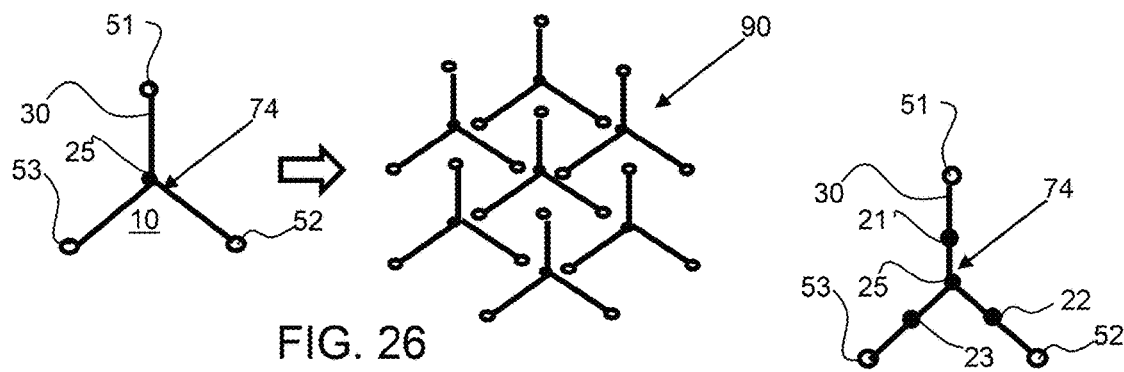
FIG. 26
FIG. 27
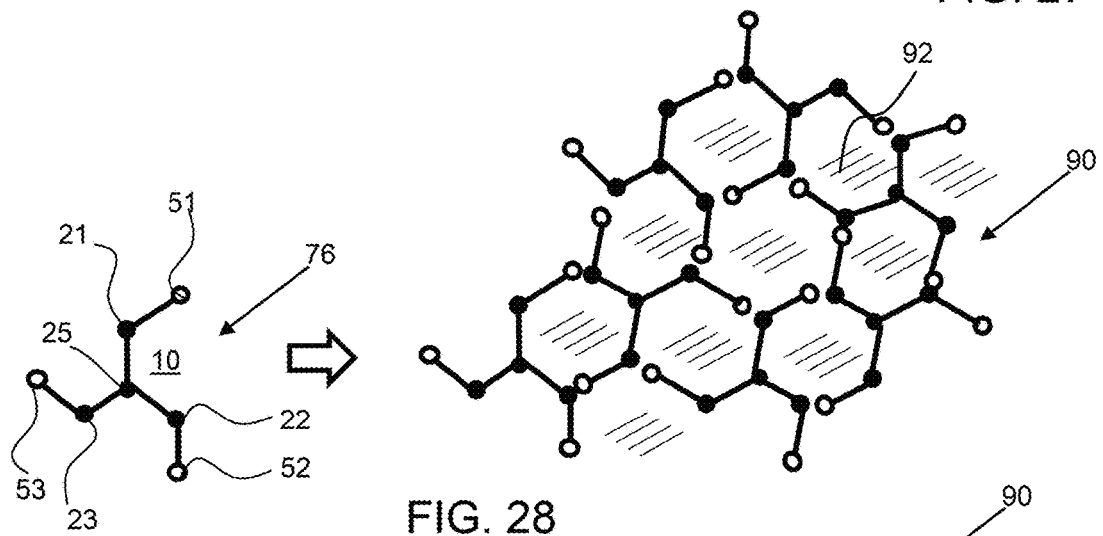
FIG. 28
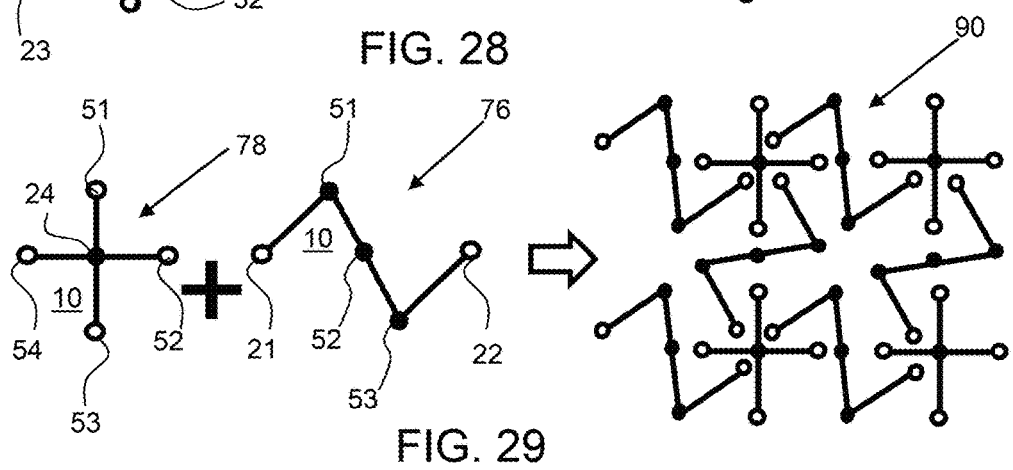
FIG. 29

COMPLIANT BIOLOGICAL SCAFFOLD

CROSS REFERENCE TO RELATED APPLICATIONS

This application is a continuation in part of PCT application No. PCT/US2020/013729, filed on Jan. 15, 2020, which claims the benefit of priority to U.S. provisional patent application No. 62/792,867, filed on Jan. 15, 2019; the entirety of each are hereby incorporated by reference herein.

BACKGROUND OF THE INVENTION

Field of the Invention invention relates to a compliant biological scaffold having a pattern of elongated apertures to enable biaxial elongation and contraction for compliance, and methods of forming said compliant biological scaffold, ex vivo or in vivo.

Background

There are a large number and types of scaffolds that are implanted into the body or topically applied to the skin. Skin grafts are commonly used for burn victims and for cosmetic surgeries. It is common to mesh these scaffolds to expand them, thereby increasing the area of coverage offered by a limited resource, and improving their compliance. Current mesh designs allow for the scaffold to be elongated in one direction at the expense of length in the perpendicular direction. This mono-direction elongation results in stress being placed on the surrounding tissue, wrinkles in the graft and surrounding tissue and in some cases rupture or tears. It significantly limits compliance when attempting to cover or modify three dimensional structures.

SUMMARY OF THE INVENTION

The invention is directed to a compliant biological scaffold having a pattern of elongated apertures to enable biaxial elongation and contraction and methods of forming said compliant biological scaffold both ex vivo or in vivo. The pattern of elongated apertures includes nodes and antinodes that enables bi-lateral expansion through expansion of the apertures and rotation of tiles configured therebetween. This renders the compliant biological scaffold compliant around complex shapes including round or curved surfaces. An exemplary compliant biological scaffold is expandable or moldable and can encourage selective contraction in specific areas; all of which systematically change the shape of the compliant biological scaffold. Altering the compliance and plasticity of a compliant biological scaffold is accomplished by introducing a plurality of elongated apertures that form a geometric pattern that enables biaxial expansion. This may be in vivo modification of living tissue including, but not limited to, skin, tendon, muscle, vessel, bone, and the like, ex vivo modification of living tissue such as sundry harvested grafts including, but not limited to, skin, bone or tendon, or modification of implantable biological devices such as plates, acellular dermal matrix, allograft, xenograft and the like. The invention is directed to a compliant biological scaffold and method of forming said compliant biological scaffold by creating the elongated apertures in a pattern as detailed herein in vivo or ex vivo.

A pattern of elongated apertures, in a closed or expanded state, or combination thereof can be formed in vivo on a bone or may be formed in a bone graft external to the body and then implanted.

A compliant biological scaffold, as used herein includes graft or biologic materials implanted or attached to biological material or tissue, and ex vivo grafts wherein biological material comprises a plurality of elongated apertures as described herein. A compliant biological scaffold may have no blood supply and be implanted to be revitalized, may be a flap wherein blood supply is left intact. A compliant biological scaffold may be tissue from the patient or from a donor that is configured with a plurality of elongated apertures, it may be tissue that is altered ex vivo with a plurality of elongated apertures or a combination of both. A compliant biological scaffold may be a non-biological material such as a fastener, screw, plate and the like and may be made out of biologically compatible materials, such metal, metal alloys, stainless steel, titanium, nitinol, bioresorbable materials, polymeric materials such as fluoropolymers and in particular polytetrafluoroethylene. Biological, as used herein, includes tissue or materials that are biologically compatible for implantation such as certain metals and alloys, polymers and the like.

In an exemplary embodiment, the elongated apertures comprise a pair of nodes centrally located on opposing sides of the aperture and between a pair of antinodes, wherein the antinodes are configured on opposing ends of the elongated aperture. The geometric pattern comprises a plurality of geometric shapes, or tiles, between the plurality of apertures. The geometric shapes or tiles have a bounded perimeter formed by the plurality of elongated apertures. An exemplary compliant biological scaffold, has a substantial portion of the elongated apertures that are configured with the antinodes proximal to one of said pair of nodes of a separate elongated aperture; wherein the antinodes are closer to one of the pair of nodes than to any other antinode. This unique arrangement of the elongated apertures produces a compliant biological scaffold material that can be biaxially expanded. During expansion of the compliant biological scaffold, the first and second nodes separate from each other while the antinodes approach each other to form an arrangement of tessellated apertures. The arrangement of the elongated apertures and tiles therebetween enables biaxial expansion with tiles rotating. Adjacent tiles that are connected through a node antinode pair counter rotate and those adjacent tiles not connected by a node antinode may pair co-rotate. This combination of tile rotation and aperture expansion enables a generally uniform biaxially expansion.

An exemplary compliant biological scaffold may be beneficial in a wide array of applications, including skin grafts, bone grafts, cardiac patches or grafts, hernia patches or grafts, organ grafts, vascular graft and stent grafts, for example. A graft may be a donor graft comprising material such as skin, bone or tissue from a donor patient, or from a donor site of the patient being treated, or may be a constructed graft, which may comprise organic donor material or layers and additional material or layers. A constructed scaffold may be synthetic scaffold made from non-donor materials such as bioresorbable material that resorb into the body over time. An exemplary scaffold material may be an in vivo scaffold made by creating the plurality of apertures and geometric pattern in the tissue directly, such as with the use of lasers. For example, a laser may be used to create a geometric pattern in skin by making the plurality of slits or apertures directly in the skin of a patient. Furthermore, an exemplary compliant biological scaffold formed in vivo in skin by imprinting the skin tissue with the plurality of apertures as described herein, is a way of programming the tissue to expand in areas where the scaffold is not expanded and contract in areas where the scaffold is expanded. Thus far, skin tissue has been made into an unexpanded compliant biological scaffold which allows for the scaffolds or tissue to expand. This can however be done in reverse; Imprinting tissue with a fully expanded scaffold and removing the material from the apertures, or selectively burning/treating said tissue within the apertures with an instrument such as a laser. This would allow for the scaffold to contract rather than expand. Such a scaffold would be useful in shortening bones to address limb length discrepancies or in common operations such as the ulnar shortening osteotomy. Furthermore, such a fully expanded scaffold could be imprinted in skin which would encourage the skin to tighten. This application may be useful in body contouring procedures including breast lifts or facial aesthetic procedures such a facelifts and neck-lifts. This technique is not limited to a scaffold made of skin. The plurality of apertures may be microscopic in scale, such as less than a millimeter in length, a micron or less to sub-micron range, or less than a micron in length.

It is also possible to imprint tissue with a differentially expanded scaffold which would precisely direct selective expansion and contraction on the same surface. An exemplary compliant biological scaffold may comprise a portion with a plurality of apertures configured to promote expansion or extension of the biological scaffold and may comprises a second portion configured to contract. A first portion of a compliant biological scaffold may comprise expanded apertures, such as expanded elongated apertures and a second portion may comprise a plurality of apertures that are not expanded. A first portion of a compliant biological scaffold may comprise unexpanded apertures, such as unexpanded elongated apertures and a second portion may comprise a plurality of apertures that are partially or fully expanded. The geometric pattern of apertures may comprise regions of elongated apertures in different degrees of expansion to promote reconfiguration of the biological material or scaffold.

Exemplary compliant biological scaffold skin grafts may be used to repair damaged skin, such as from burns, chemical damage, cuts or abrasions, for example. An exemplary compliant biological scaffold skin grafts may provide compliance in highly elongated areas, including the elbows, knees and the like. As mentioned, compliant biological scaffold skin grafts may be used in cosmetic procedures such as cleft palate surgeries and the like.

An exemplary compliant biological scaffold bone graft may be used to aid in the restructure of bone. In an Ilizarov technique, the two ends of the bone are slowly distracted and an in-vivo compliant biological scaffold bone may be created along a portion of the bone to improve the compliance of the bone and increase the rate of distraction. Alternatively, an in-vivo compliant biological scaffold bone may be used along a portion of the bone, instead of or in conjunction with a full thickness osteotomy to improve the compliance of the bone. Improved compliance may enable more strain of the for a given amount of stress or force on the compliant biological scaffold. The Ilizarov technique is used where one bone is shorter than another through injury, or birth. In some cases, the Ilizarov technique is used for cosmetic reasons, such as to make a person taller. In some cases, this technique may not just augment but actually obviate the need for the Ilizarov technique. These applications fall under the general category of osteogenic distraction that involves making complete osteotomies in bone to be expanded. By transforming the same bone into a biologic scaffold as described, using this plurality of apertures, such distraction techniques mat not require full osteotomies, or separation of the bone being altered, but rather a plurality of smaller partial osteotomies that may greatly reduce distraction times, and increase safety by creating inherently more stable expansion constructs.

An exemplary compliant biological scaffold bone graft may be used in a Cranioplasty technique to repair abnormal skull shapes. An ex-vivo compliant biological scaffold bone graft may be produced in a skull using a laser, bone scalpel or other suitable method to produce apertures through the skull or through a portion of the skull. This ex-vivo compliant biological scaffold bone may allow expanding or contracting of the cranial vault to treat pediatric growth malformations. In addition, this ex-vivo compliant biological scaffold method may be a more effective treatment to treat increased intra cranial pressure in adults from such conditions as hydrocephalus, intracranial mass or acute or chronic trauma. It is also possible to create a compliant meshed scaffold from the cranial vault in vivo without extricating the skull or removing it from its blood supply. Such techniques may augment current so called "strip craniectomy" procedures.

An exemplary compliant biological scaffold of bone may be a bone graft, osseous free flap, or vascularized in vivo bony structure having elongated apertures formed therein ex vivo or in vivo for osteoplasty. Osteoplasty is the branch of surgery concerned with bone shaping, repair, or bone grafting. It is the surgical alteration or reshaping of bone and may be used to relieve pain associated with metastatic bone disease. An in vivo bone compliant biological scaffold may include a pattern of elongated apertures in a closed configuration and/or in an expanded configuration, wherein the elongated apertures are an expanded scaffold. For example, for ulna shortening, a bone may be configured with a pattern of elongated apertures in an open state to encourage the bone to shorten. Note that an osteoplasty utilizing a pattern of elongated apertures, as described herein, may be used to shorten, lengthen, twist or otherwise remodel bone. An exemplary compliant biological scaffold may be a bone graft or flap having elongated apertures formed ex vivo or in vivo respectively for osteoplasty.

These scaffolds may be part of computer guided osteotomy with pre bent plates for corrective osteotomies. Currently these osteotomies are a series of pre-planned full thickness bone cuts that then allow for the bones to be reconfigured in a predetermined way and affixed to a pre-bent plate, which may be computer aided in terms of determination of the pattern of osteotomies and/or control of a cutting implement, such as a laser, drill, saw, or knife to create the pattern of osteotomies. The biologic scaffold can render bones compliant and moldable, using a predetermined pattern of apertures, expanded, partially expanded, unexpanded or a combination thereof, obviating or reducing the need for full thickness osteotomies, and can be a part of the computer guided osteotomy and reshaping process. This is particularly valuable in face/mandible/skull reconstruction or correction and complex limb reconstruction/corrections.

An exemplary compliant biological scaffold has a plurality of elongated apertures that are linear apertures extending between a pair of antinodes, or from a first antinode to a second antinode. Exemplary elongated apertures have a length to width ratio in a non-elongated state of about two or more, about three or more, about five or more and any range between and including the ratios provided. The length of the apertures may be microscopic such as less than a millimeter in length, a micron or less to sub-micron range, or less than a micron in length. An exemplary compliant biological scaffold may consist of linear elongated apertures which may all be microscopic as defined herein.

An exemplary compliant biological scaffold comprises a plurality of elongated apertures configured in a pattern to produce geometric shapes or tiles. In an exemplary embodiment, a substantial portion of the elongated apertures, such as 50% or more and preferably 80% or more, are arranged orthogonally to each other, wherein a first elongated aperture is orthogonal to a second elongated aperture configured on a first antinode end of said first elongated aperture. In an exemplary embodiment, a compliant biological scaffold consists essentially of, such as at least 90% or more, elongated apertures that are arranged orthogonally to each other. A geometric pattern having elongated apertures that are arranged orthogonally to each other includes a first elongated aperture having a first antinode end that is proximal to a first node of a second elongated aperture, and the length axis of the first and second elongated apertures are substantially orthogonal to each other, or within about 20 degrees or orthogonal.

In an exemplary embodiment, a compliant biological scaffold comprises a plurality of cross-shaped apertures, wherein a length axis of the first elongated aperture extends through a first node of the second elongated aperture. A cross-shaped apertures comprises four antinodes on the extended ends of the two intersecting elongated apertures. An exemplary cross-shaped aperture has a length axis of a first elongated aperture that extends centrally through the second elongated aperture, such as within about 20% of the center of the length of the second elongated aperture. The length of the two elongated apertures of the cross-shaped aperture may be substantially the same or within about 20% of each other. A symmetric cross-shaped aperture comprises two elongated apertures of substantially the same length that intersect with each other centrally, as defined herein.

In an exemplary embodiment, a compliant biological scaffold comprises plurality of Y-shaped apertures, having three separate extension that extend from a central point. An exemplary Y-shaped aperture comprises three extensions that are substantially the same length and these three extensions may extend substantially an equidistant circumferentially from each other, wherein each extends from the center point about 120 degrees apart, such as within about 100 to 140 degrees.

An exemplary compliant biological scaffold comprising two pairs of nodes configured between antinodes along said elongated aperture. This type of elongated aperture forms a rectangle aperture upon expansion of the nodes from each other. A first pair of nodes forms one side of the rectangular aperture with a first antinode configured therebetween and the second pair of nodes forms a second and opposing side of the rectangle with the second antinode therebetween.

An exemplary compliant biological scaffold comprises a geometric pattern of elongated apertures and geometric shapes wherein a substantial portion of the elongated apertures are arranged in a I-configuration. In an I-configuration, a first elongated aperture is substantially orthogonal, within about 20 degrees of orthogonal, to a second elongated aperture configured on the first antinode end of said first elongated aperture and wherein said first elongated aperture is substantially orthogonal to a third elongated aperture configured on the second antinode end of said first elongated aperture.

An exemplary compliant biological scaffold comprises a geometric pattern of elongated apertures and geometric shapes wherein the geometric shape has a plurality of corners and wherein each of said plurality of corners are bound by a node of separate elongated apertures. An exemplary compliant biological scaffold comprises a geometric pattern of elongated apertures and geometric shapes wherein the geometric shape is a rectangle and wherein the corners of the rectangle are bound by a node of four separate elongated apertures. An exemplary compliant biological scaffold comprises a geometric pattern of elongated apertures and geometric shapes wherein the geometric shape is a triangle and wherein the corners of the triangle are bound by a node of three separate elongated apertures, which may be a side of an adjacent triangular geometric shape. An exemplary compliant biological scaffold comprises a geometric pattern of elongated apertures and geometric shapes and may comprise a single geometric shape, or two or more geometric shapes. An exemplary compliant biological scaffold comprises a geometric pattern of elongated apertures and geometric shapes and may consists essentially of a single geometric shape, such as a rectangle or triangle.

A cutting template may be used to indicate the geometric pattern of elongated apertures for cutting in the biological material which may be in vivo or ex vivo. In an exemplary embodiment and cutting template is translucent or transparent and placed over tissue in vivo, such over a fracture in bone or over a wound in tissue. A medical profession may then form the pattern by cutting through the template into the bone or tissue, and may cut only around the fracture or the wound. A cutting template may have an adhesive on one side for adhering to the biological material. In ex vivo biological material, a cutting template may be applied and used manually or may guide an automated cutting implement, such as an automatically controlled laser cutter.

Definitions

An adjacent tile portion is a tile portion connect to another tile portion by a connection portion.

A substantial portion as used herein means at least 50% or more and preferably 80% or more.

In vivo, as used herein with respect to formation of geometric pattern of elongated apertures, means forming said geometric pattern of elongated apertures in biological tissue native to the patient and in or a part of the patient's body; in vivo may be part of a surgical procedure.

Ex vivo, as used herein with respect to formation of geometric pattern of elongated apertures, means forming said of geometric pattern of elongated apertures in biological material outside of a patient's body.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

FIGS. 22 to 29 show geometric patterns of apertures in compliant biological scaffold.

FIG. 22 shows a geometric pattern of I-shaped apertures to form a compliant biological scaffold and the expanded compliant biological scaffold.

FIG. 23 shows a geometric pattern of I-shaped apertures to form a compliant biological scaffold and the expanded compliant biological scaffold.

FIG. 24 shows a geometric pattern of I-shaped apertures to form a compliant biological scaffold and the expanded compliant biological scaffold.

FIG. 25 shows a geometric pattern of I-shaped apertures having two antinodes between a first and second node.

FIG. 26 shows a geometric pattern of Y-shaped apertures.

FIG. 27 shows a Y-shaped aperture having nodes between the intersection of three legs of the Y-shaped aperture and an tri-node at the intersection.

FIG. 28 shows a geometric pattern of skewed shaped apertures.

FIG. 29 shows a geometric pattern including cross-shaped apertures between skewed shaped apertures.

Figure 1:
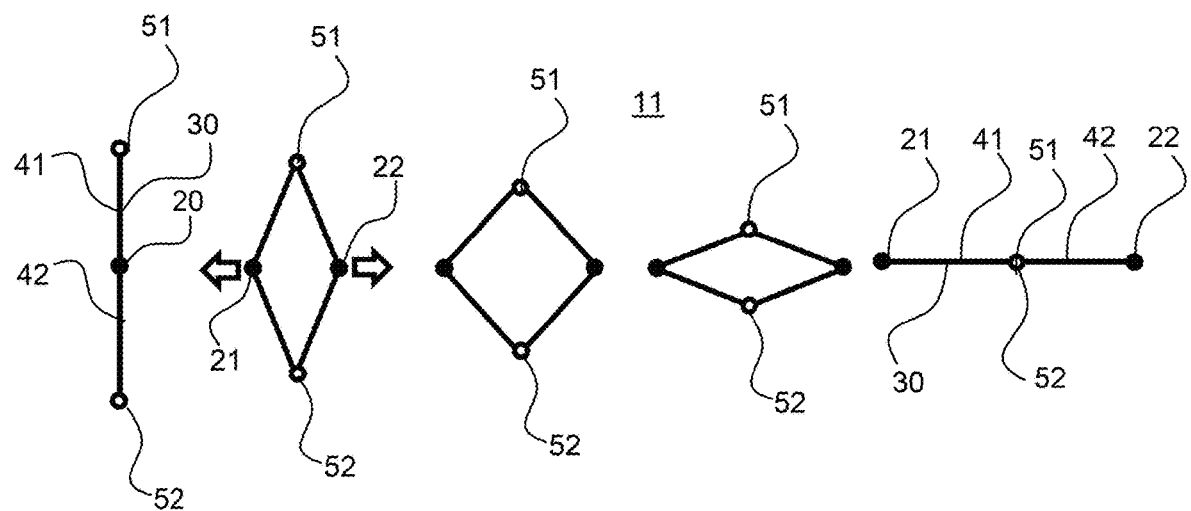
FIG. 1 shows an exemplary elongated aperture having a pair of nodes configured on opposing extended ends of the elongated aperture and a pair of antinodes configured centrally between the extended ends and on opposing sides of the elongated aperture.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Throughout the figures nodes in an elongated aperture are depicted as circles and antinodes are depicted as black circles.

A compliant biological scaffold, as used herein, is a material that is biologically compatible and that is compliant to enable expansion or contraction along the plurality of apertures and includes, but is not limited to, ex vivo biologically material such as bone, muscle, skin, organ tissue and the like, biologically tissue or material from a secondary organism, as well as synthetic biological material including polymeric graft materials, such as fluoropolymers, bioresorbable materials, metal and metal alloys including titanium, stainless steel, shape memory metal alloys including, NiTi alloys or Nitinol and the like. A compliant biological scaffold may be formed ex vivo by the formation of the plurality of elongated apertures in tissue or bone for example.

As shown throughout the figures, a node is represented as an black circle and an antinode is represented as a open circle.

As shown in FIG. 1, an exemplary graft 11 comprises an elongated aperture 30 comprising a pair of nodes 20, or node pair configured centrally between two antinodes 51, 52. A pair of nodes is an arrangement of two nodes next to each other on opposing sides of an elongated aperture. This pair of nodes comprises node 21 and 22. The elongated aperture has a first extension 41 extending from the node pair 20 to the first antinode 51 and a second extension 42 extending from the node pair to the second antinode 52. As the compliant biological scaffold is elongated the nodes 21, 22, of the elongated aperture 30 separate to form a diamond. As the compliant biological scaffold is stretched further the nodes separate further and the antinodes contract toward each other whereby the nodes become antinode and the antinodes become nodes. As the compliant biological scaffold is elongated further, the antinodes approach one another and the nodes are fully extended apart. This simple elongated aperture produces a maximally expanded square aperture when nodes and antinodes are equidistant. Further expansion of the nodes in the same relative direction leads to contraction of this maximum open area of the aperture with the antinodes moving closer to each other until in essence the nodes have become antinodes and the antinodes have become nodes. This is a reason why apertures not connected by node/antinode pairs contract in one direction when expanding in another.

Figure 2:
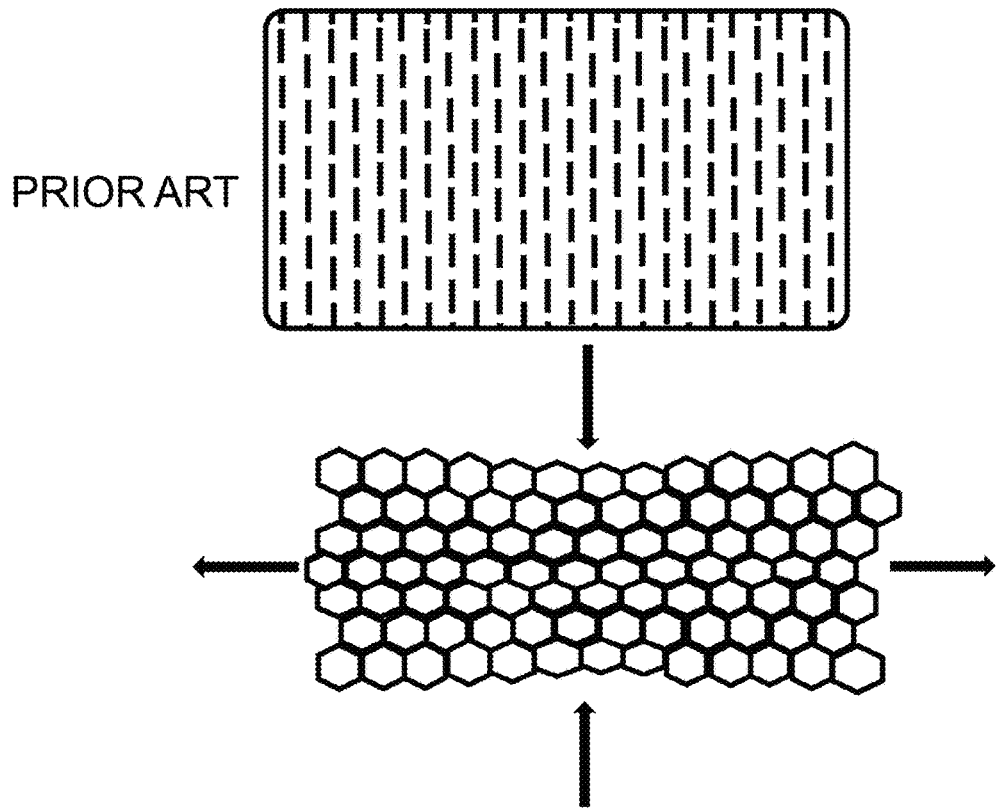
FIG. 2 shows an exemplary graft having an arrangement of elongated apertures that results in contraction of the graft when elongated.

As shown in FIG. 2, a graft having an arrangement of apertures aligned with each other can be elongated but this causes contraction in the opposing direction. The nodes separate and the antinodes contract causing the graft material to neck in, or contract, in a direction perpendicular to the direction of elongation.

Figure 3:
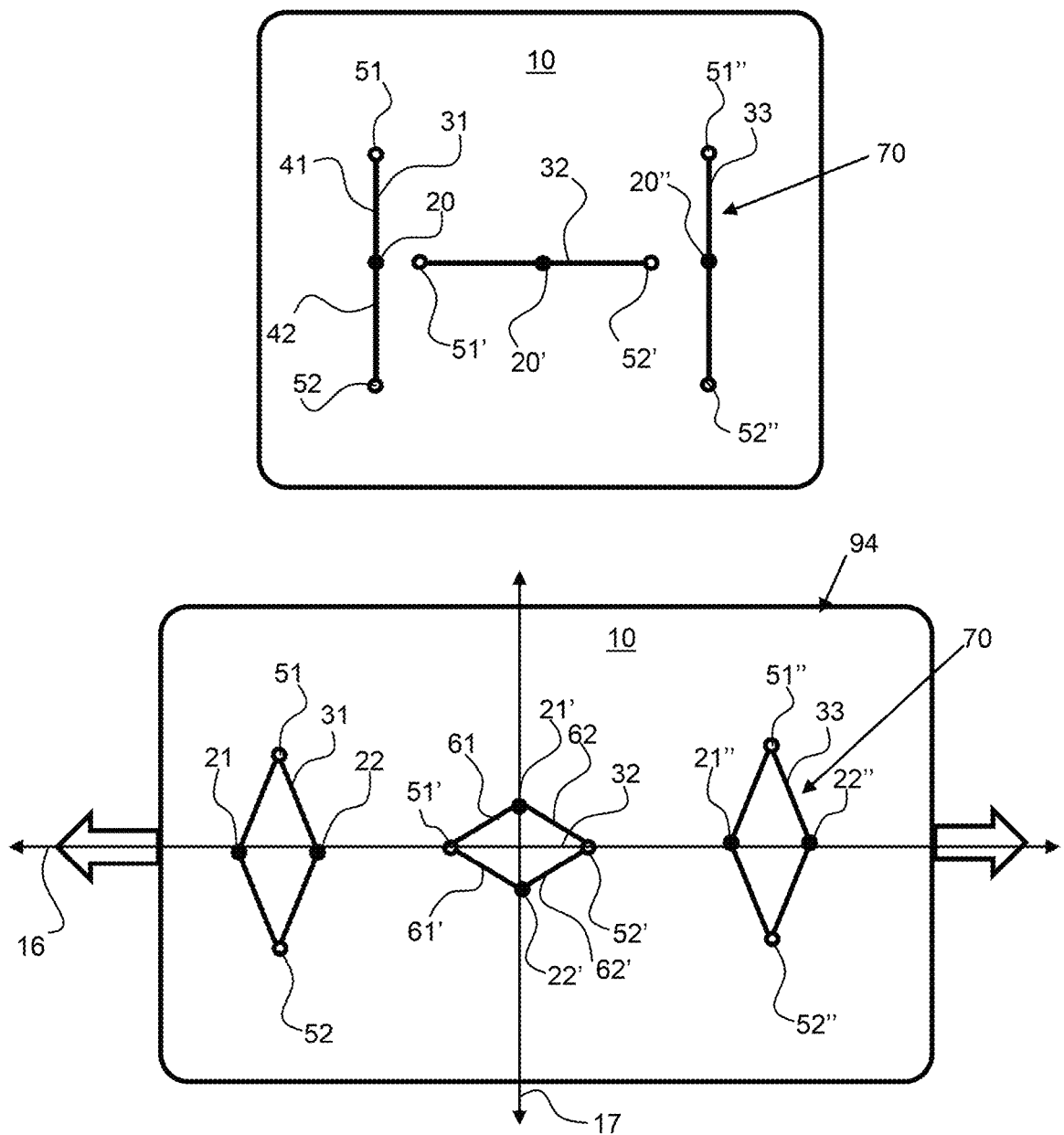
FIG. 3 shows an exemplary compliant biological scaffold having elongated apertures configured with the nodes of a first elongated aperture proximal to the antinodes of an adjacent elongated aperture.

FIG. 3 shows an exemplary graft material 10 with an exemplary geometric pattern of I-shaped elongated apertures 70 comprising elongated apertures 31, 32, and 33, each having nodes 21, 22 configured between a pair of antinodes 51, 52 in a linear elongated aperture. The top figure shows the compliant biological scaffold without tension or elongation. The bottom figure shows the graft material being elongated, as indicated by the bold arrows. As the material is elongated, the nodes 21, 22 of the two outer elongated apertures 31 and 33, separate in the direction of the elongation, or the elongation axis 16. The nodes of the center elongated aperture 32 also separate as the sides 61, 62, and 61', 62' around the antinodes 21' and 22', respectively, separate in the elongation axis. As the sides separate, the nodes 21', 22' also separate in the cross-elongation axis 17. The configuration of the antinodes of the center elongated aperture 32 proximal to the pairs of nodes 20, 20' and 20", of the outer elongated apertures 31, 33, causes this more uniform elongation of the compliant biological scaffold material without necking or contraction in the cross-elongation axis. The bottom graft material 10 is an expanded scaffold 94.

Figure 4:
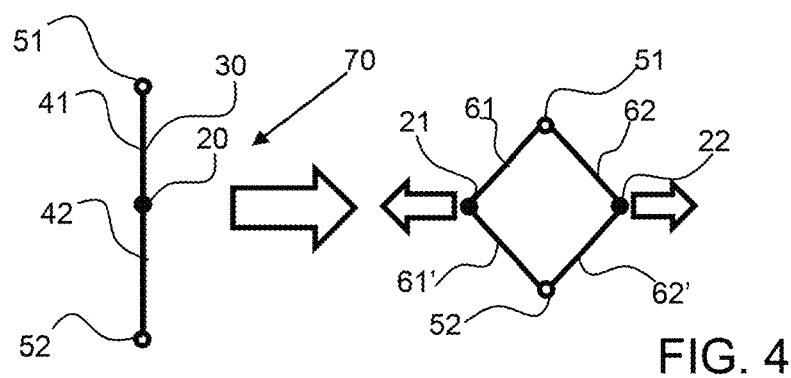
FIGS. 4 to 9 shows a plurality of elongated aperture configurations with nodes configured between antinodes.

FIG. 4 shows an exemplary linear elongated aperture 30 having a pair of nodes 20 configured centrally along the aperture and pair of antinodes 51, 52 configured on opposing ends of the aperture. A first antinode 51 is configured at the extended end of a first extension 41 from the pair of nodes and a second antinode 52 is configured at the extended end of a second extension 42 from the pair of nodes. As shown in the expanded version of the elongated aperture, a square shaped opening or aperture may be formed from the elongated aperture when elongated as indicated by the bold arrows. The two sides 61, 62, and 61', 62' of the elongated aperture between the nodes and antinodes form the sides of the rectangle.

Figure 5:
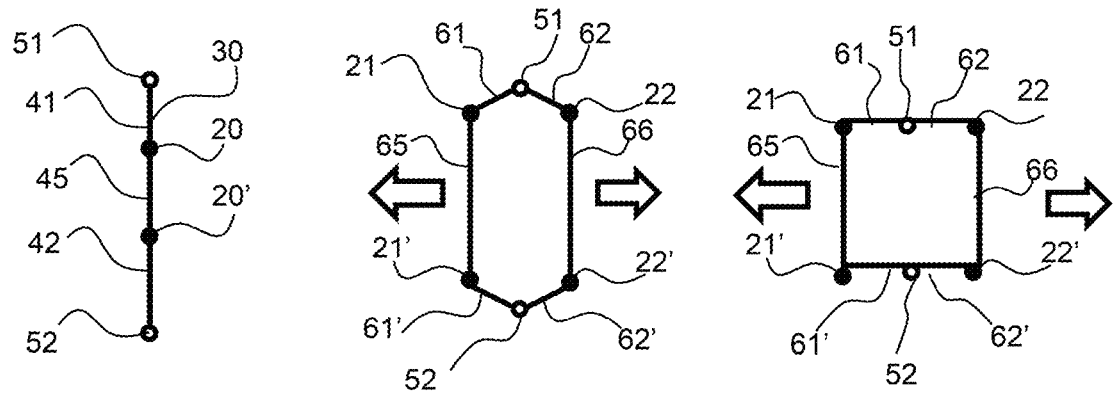

As shown in FIG. 5, an exemplary elongated aperture 30 has two pairs of nodes 20, 20' configured between two opposing antinodes 51, 52. Again, this is a linear elongated aperture having a first extension 41 from the first pair of nodes 20 to the first antinode 51 and a second extension 42 from the second pair of nodes 20' to the second antinode 52. A node extension 45 extends between the two pairs of nodes 20, 20'. As the elongated aperture is elongated, a hexagon shaped aperture is formed initially that may form into a square or rectangle, depending on the lengths of the extensions and node extensions. A first side 61 and a second side 62 of the aperture is formed on either side of the antinode 51 and a first side 61' and a second side 62' of the aperture is formed on either side of the antinode 52. A first node side 65 and second node side 66 are formed between the two pairs of nodes, or more specifically, between nodes 21 and 21' and nodes 22 and 22', respectively.

Figure 6:
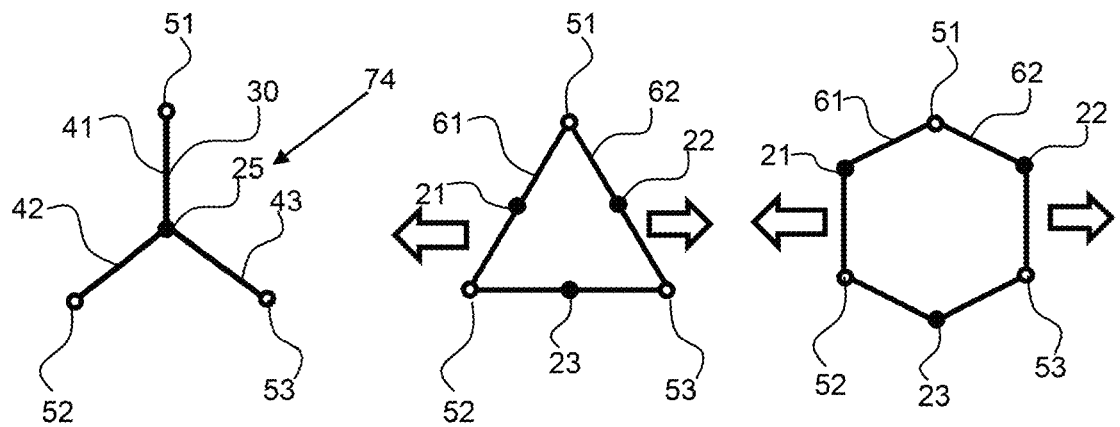

As shown in FIG. 6, an exemplary Y-shaped aperture 74 has three antinodes configured around a centrally configured tri-node 25 which includes node 21, 22 and 23. Each of the antinodes 51, 52, 53 is configured at the extended end of an extension that extends from the tri-node 25. A first antinode 51 is configured at the extended end of a first extension 41 from the tri-node, a second antinode 52 is configured at the extended end of a second extension 42 from the tri-node and a third antinode 53 is configured at the extended end of a third extension 43 from the tri-node. The three extensions are configured at a substantially equal circumferential distance from each other, or about 120 degrees apart plus or minus 20 degrees and more preferably within 10 degrees of 120 degrees. As this elongated aperture is elongated, as indicated by the bold arrows, the nodes 21, 22, and 23 separate from each other to form a triangular shaped aperture. As the elongated aperture is elongated further, a hexagonal shaped aperture is formed. This elongated aperture provides a high level of compliance in multiple directions. A side extends between each antinode and the two adjacent nodes, such as sides 61 and 62 extending between antinode 51 and nodes 21 and 22.

Figure 7:
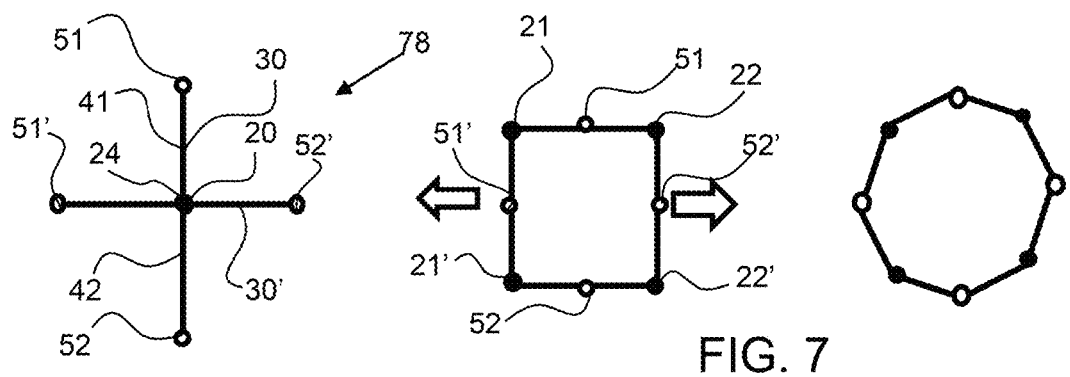

As shown in FIG. 7, a cross-shaped aperture comprises two elongated apertures that intersect at a node 20, or quad node 24. The quad node 24, being a configuration of four nodes located proximal to each other, separates into these four nodes, 21, 21', 22, and 22' to form a rectangle upon expansion, as indicated by the bold arrows in the center figure. The antinodes 51, 52, 51', 52' are configured between the nodes. Further expansion results in a polygon having eight surfaces. The nodes are indicated by solid small circles while the antinodes are indicated by small circles.

Figure 8:
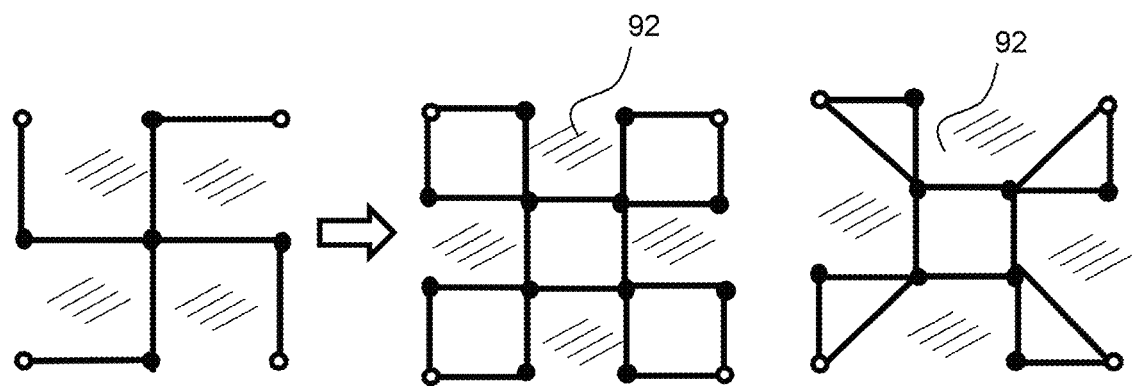

As shown in FIG. 8, a more complex aperture comprises a generally cross-shaped aperture with extensions from each of the extended ends of the cross. This complex shaped aperture produces tiles 92 within the quadrants of the apertures.

Figure 9:
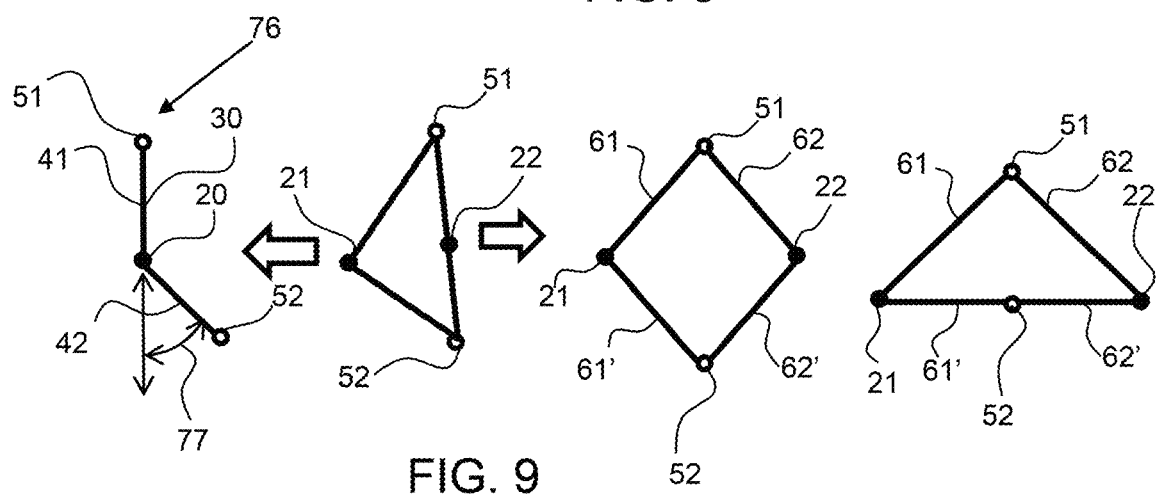

As shown in FIG. 9, a skewed elongated aperture 76 comprises a first extension 41 from a pair of nodes 20 and a second extension 42 from the pair of nodes that extends at an offset angle 77 from alignment with the first extension, whereby they first and second extensions are not aligned, as is the case with a linear elongated aperture shown in FIG. 1. As this skewed elongated aperture is expanded a triangle is initially formed, and then a rectangular shaped polygon aperture is formed; note that the sides may not be equal length and the angles between the sides may not be 90 degrees as is the case with a rectangle. Further expansion of the aperture results in a triangle.

Figure 10:
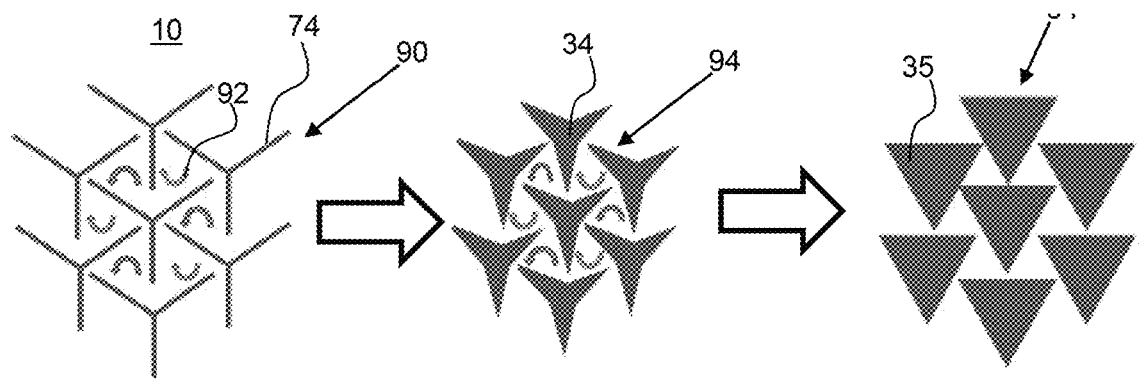
FIG. 10 shows a compliant biological scaffold material having an exemplary geometric pattern of elongated apertures having three antinodes configured at the antinode ends of separate extensions from the pair of nodes and the geometric patterns formed when the graft material is elongated.

As shown in FIG. 10, an exemplary compliant biological scaffold 10 comprises a plurality of Y-shaped apertures 74 configured with the antinodes proximal to a node to produce geometric shapes or tiles 92, therebetween. As the graft 10 is elongated the apertures open up and the tiles therebetween rotate to enable biaxial expansion. The tiles that are connected by a node antinode pair counter rotate and those not connected by a node antinode pair co-rotate. This combination of tile rotation and aperture expansion enables a generally uniform biaxially expansion. As shown the plurality of Y-shaped apertures 74 expand to partially expanded apertures 34 before being further expanded into fully expanded apertures 35.

Figure 11:
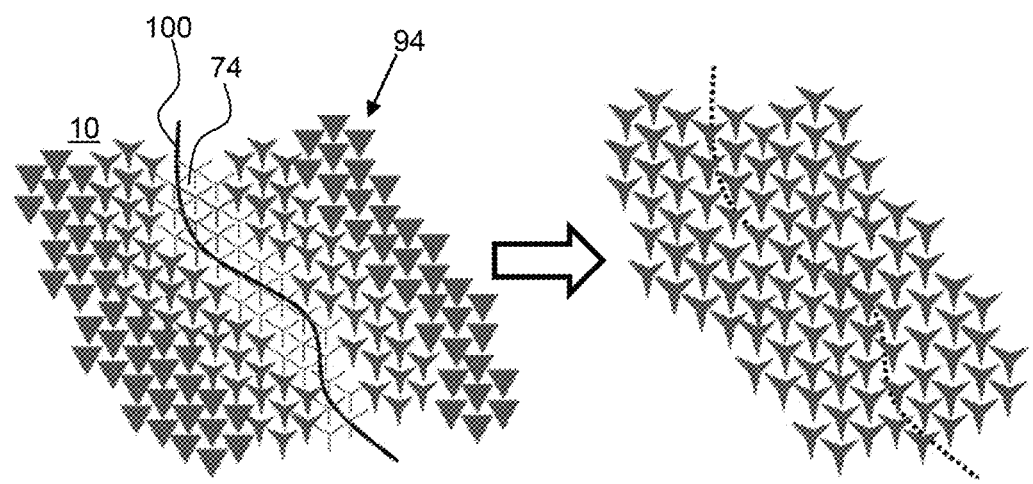
FIG. 11 shows a compliant biological scaffold material having an arrangement of apertures to enable both expansion and contraction around the contours of a wrinkle to diminish the wrinkle.

As shown in FIG. 11, an exemplary in-vivo scaffold comprises a plurality of Y-shaped apertures 74 configured with the antinodes proximal to a node to produce geometric shapes or tiles 92, in tissue, such as skin. This in-vivo scaffold is configured around a wrinkle 100 in the skin. Over time, as indicated by the bold arrow, the apertures that are unexpanded open up, and the fully expanded elongated apertures contract; the tiles rotate to relieve the wrinkles, or indented scars, and diminish the blemish form the surface of the skin. Such a differentially expanded scaffold could be imprinted onto the surface of tissue or skin, with potentially a Laser or specifically designed cutting device that would remove the tissue within the fully expanded areas, essentially pre-programming the scaffold to precisely alter its shape as tissue regenerates. This kind of tissue programming can be performed ex vivo or in vivo on a variety of grafts/flaps/tissues/or biocompatible implants. Such a technique could program blood vessels to shrink, such as varicose veins, or to expand, such as stenotic arteries. FIG. 11 diagrams an exemplary compliant biological scaffold 10 that is differentially expanded as shown on the left side of the bold arrow; wherein some of the elongated apertures or a portion of the plurality of apertures are expanded to a different degree than other elongated apertures. The plurality of elongated apertures proximal to the wrinkle are not expanded, or expanded to a lesser amount than the plurality of elongated apertures configured distal from the wrinkle. The elongated apertures proximal the wrinkle may expand while the expanded scaffold 94, elongated apertures may contract. In this way the scaffold is programmed to selectively alter its own structure or function, including the tissues that the scaffold is directing the regeneration thereof. The central area is programmed to expand while the edges, or outer portions, are programmed to contract. As the scaffold equilibrates, such that the surface reaches a state of homogenous expansion, indicated by the right side of FIG. 11, the edges contract and the center expands. This technique can be used to treat indented wrinkles 100 or scars in skin.

Figure 12:
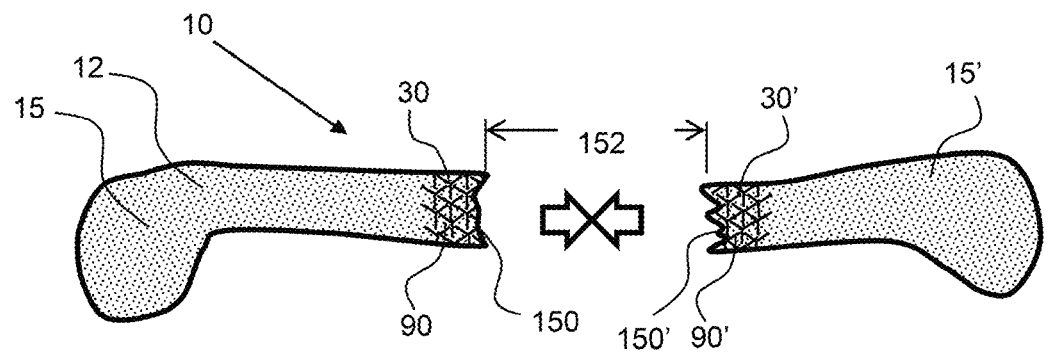
FIGS. 12 to 14 show an exemplary compliant biological scaffold configured in an ex vivo bone that is fractured, wherein a geometric pattern of apertures is formed proximal the first and second fractured ends of the bone to allow expansion of the bone.
Figure 13:
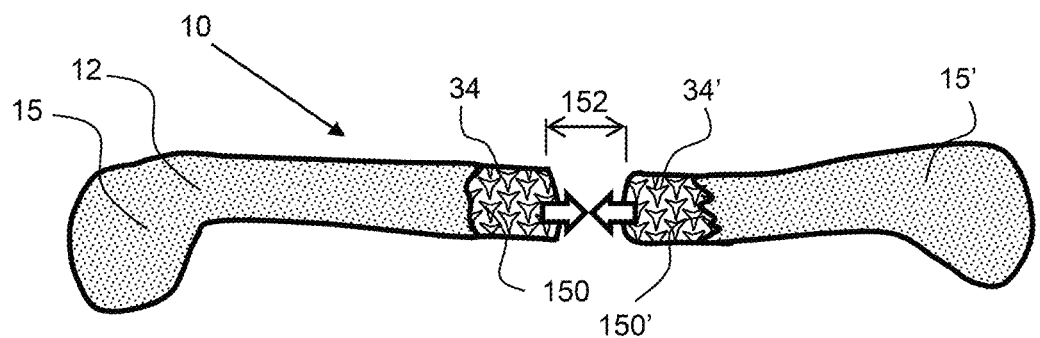
Figure 14:
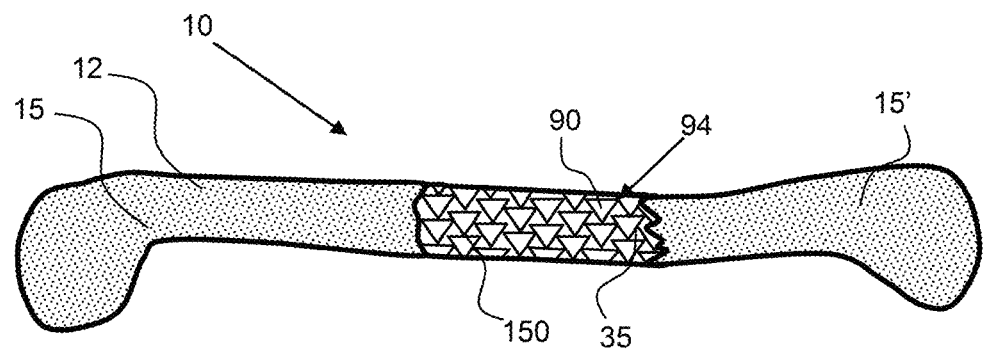

Referring now to FIGS. 12 to 14, an exemplary compliant biological scaffold 10 is configured in an in vivo biological scaffold material 12, bone 15, 15', that is fractured. A geometric pattern of apertures 90, 90' is formed proximal the first fractured end 150 and second fractured end 150' of the bone to allow expansion of the bone. As shown in FIG. 13, the elongated apertures 30, 30' of the geometric pattern of apertures 90, 90', respectively, has expanded to form partially expanded elongated apertures 34, 34' thereby allowing expansion of the bone to reduce the fracture gap 152. As shown in FIG. 14, the elongated apertures are now fully expanded elongated apertures 35 and the fractured bone is now repaired through expansion of the bone facilitated by the geometric pattern of apertures 90 formed therein, which form an expanded scaffold 94 in the bone.

Figure 15:
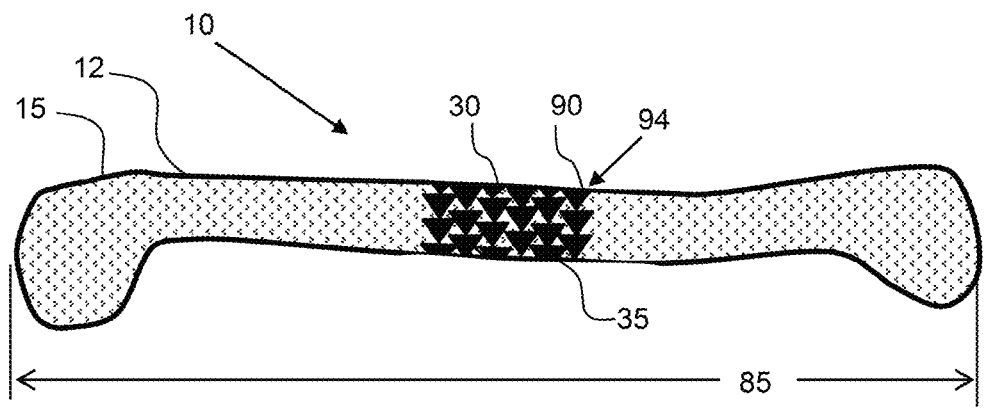
FIGS. 15 to 17 show an exemplary compliant biological scaffold configured in an ex vivo bone for osteoplasty, wherein the bone is shortened by the formation of an expanded scaffold in the bone to cause the bone to shorten.
Figure 16:
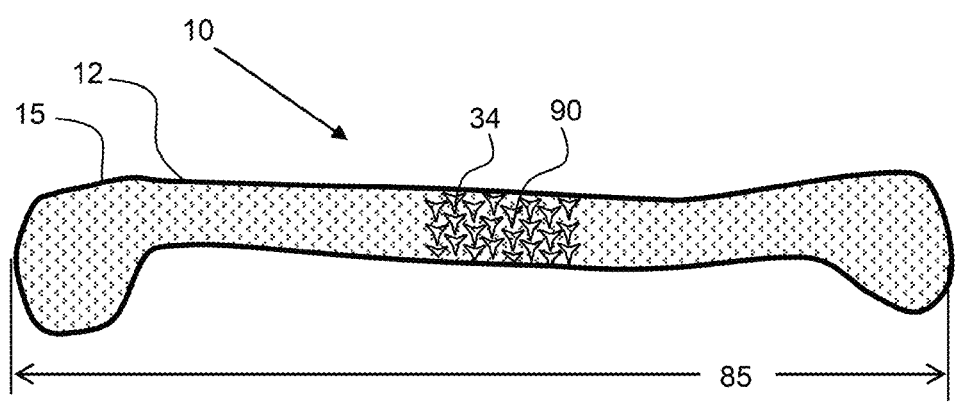
Figure 17:
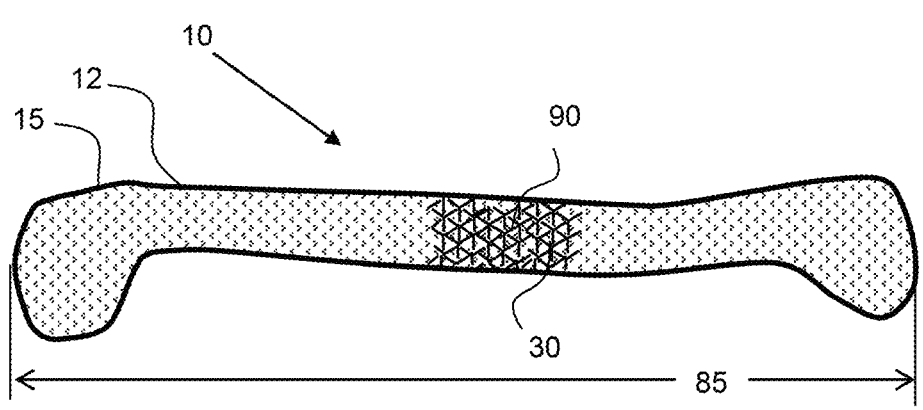

Referring now to FIGS. 15 to 17, an exemplary compliant biological scaffold 10, in this case an expanded scaffold 94, is formed in vivo in a bone 15 to cause the bone to shorten. FIG. 15 shows the pattern of expanded elongated apertures 30 which include expanded apertures 35 formed in the bone and FIG. 16 shows the scaffold reduced in size due to the shortening of the bone and FIG. 17 shows a shortened bone as a result of the formation of a pattern of an expanded scaffold in the bone. The length of the bone 85 is reduced from FIG. 15 to FIG. 17.

Figure 18:
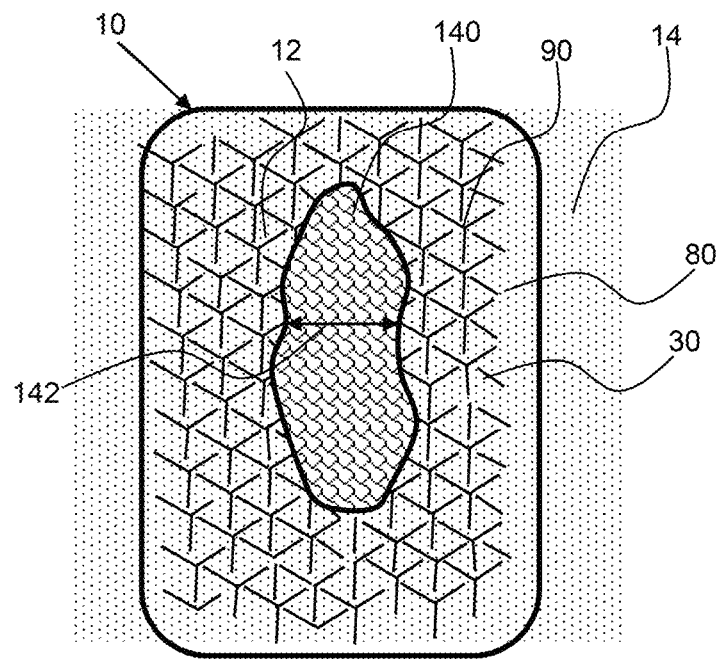
FIGS. 18 and 19 show an exemplary compliant biological scaffold configured in ex vivo tissue, wherein a geometric pattern of apertures is formed around the wound to allow the wound to close with reduced scarring.
Figure 19:
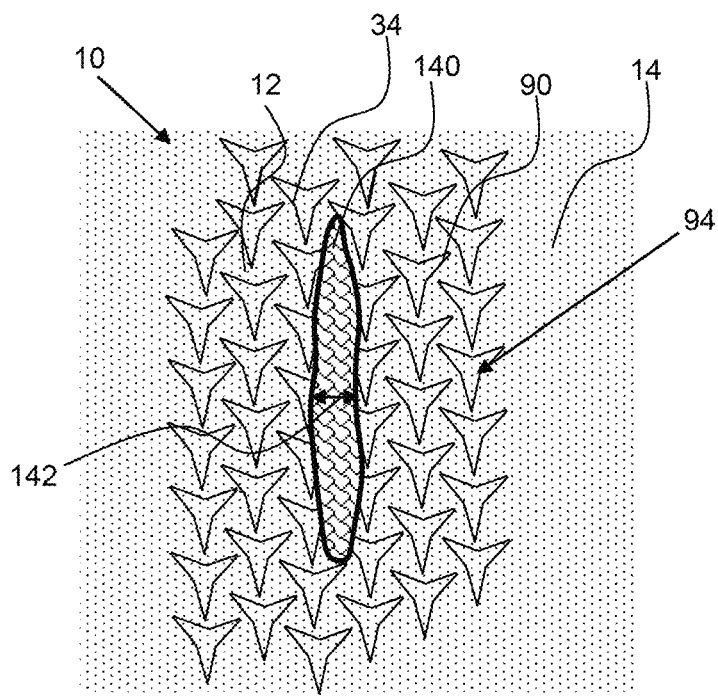

Referring now to FIGS. 18 and 19, an exemplary compliant biological scaffold 10 is configured in an in vivo biological scaffold material 12, tissue 14. A cutting template 80 is configured over a wound in tissue to provide the geometric pattern of apertures 90 for cutting in said tissue. A medical professional may cut the pattern in the tissue around the wound 140 to allow for expansion of the tissue to close the wound and reduce scaring. A geometric pattern of apertures 90 is formed in the tissue around the wound 140 to allow the wound to close with reduced scarring. The plurality of elongated apertures 30 formed are non-expanded apertures as shown in FIG. 18. As shown in FIG. 19, the cutting template is removed and over time, the geometric pattern of apertures 90 expands forming partially expanded elongated apertures 34 to allow the tissue to expand and thereby enable wound closure by the expanded scaffold 94. The wound opening gap distance 142 is reduced from FIG. 18 to FIG. 19 as shown.

Figure 20:
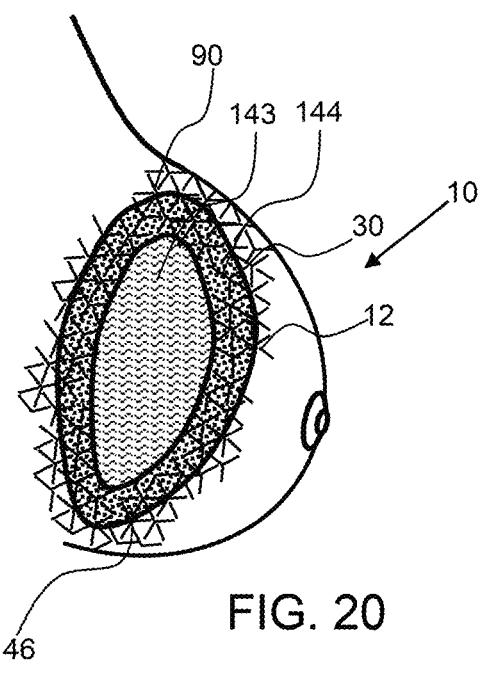
FIGS. 20 and 21 show an exemplary compliant biological scaffold configured in ex vivo breast tissue, wherein a geometric pattern of apertures is formed around a breast implant to reduce or eliminate a stiff capsule formed around the breast implant.
Figure 21:
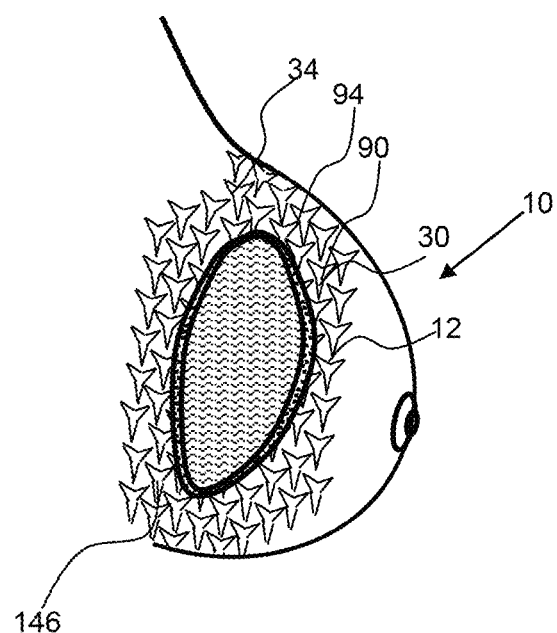
Figure 22:
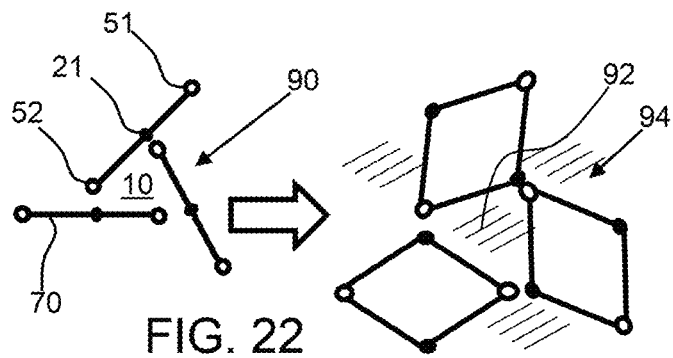
Figure 23:
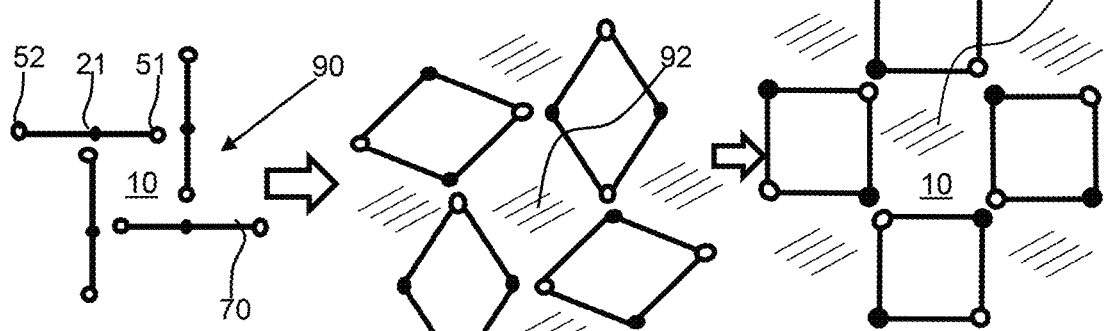
Figure 24:
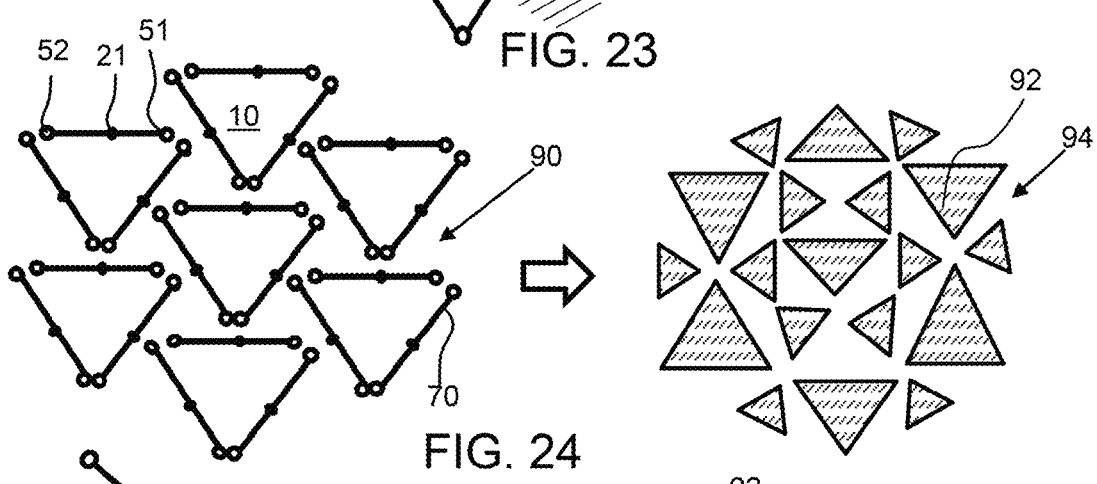

Referring now to FIGS. 20 and 21, an exemplary compliant biological scaffold 10 is configured in in-situ graft material or in-vivo capsules or material already engrafted previously and modified in vivo biological scaffold material 12, breast tissue 146. A geometric pattern of apertures 90 is formed in the stiff capsule 144 of tissue formed around a breast implant 143. The geometric pattern of apertures 90 breaks up the stiff capsule and allows the tissue to reconfigure as shown in FIG. 21, wherein the geometric pattern of apertures 90 is expanded to form expanded elongated apertures 35 or an expanded scaffold 94. This may be performed on tissue around the graft or capsule of on the graft or capsule itself. In addition, grafts may be modified in-situ before they are placed in the breast, around a breast implant or within or upon an already formed breast capsule.

Figure 25:
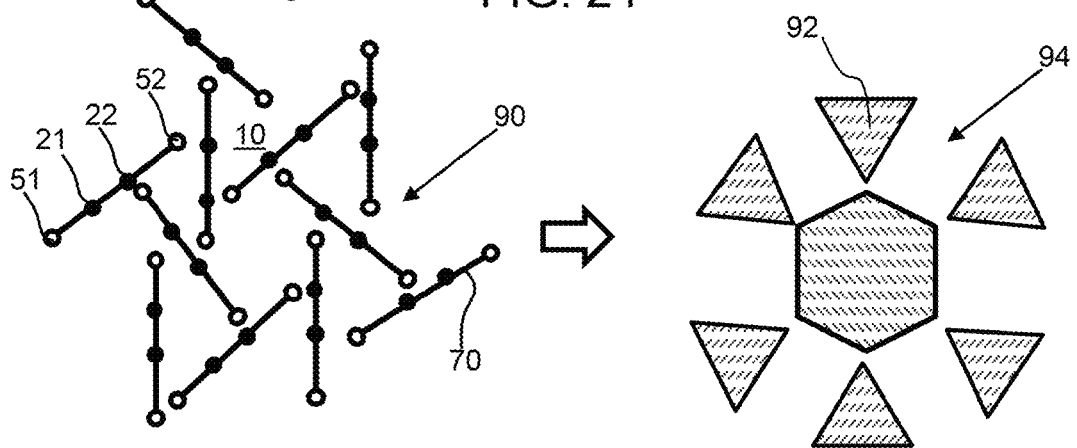

FIGS. 22 to 29 show geometric patterns of apertures 90 in compliant biological scaffold 10. The nodes are indicated by solid small circles while the antinodes are indicated by small open circles. FIGS. 22 to 25 show a geometric pattern of apertures 90 that are an arrangement of I-shaped apertures 70 to form a compliant biological scaffold 10 and the expanded compliant biological scaffold 94. The tiles 92 between the elongated apertures are shown after expansion, as indicated by the bold arrow. FIG. 25 shows a geometric pattern of I-shaped apertures 70 having a first node 21 and a second node 22 between a first antinode 51 and second antinode 52.

FIG. 26 shows a geometric pattern of Y-shaped apertures 74 in biological scaffold 10 and configured in a geometric pattern of apertures 90 with antinodes from a first Y-shaped aperture being proximal to and node of a second Y-shaped aperture. Note that the extensions from the proximally located nodes and antinodes may be substantially in alignment, such as within about 20 degrees of each other and preferably within about 10 degrees of each other.

FIG. 27 shows a Y-shaped aperture 74 having an antinode 51, 52 and 53 at the extended end of the extensions of the elongated apertures 30 and nodes 21, 22 and 23 between the intersection of three legs of the Y-shaped aperture and an tri-node 25, at the intersection of the extensions from the antinodes.

FIG. 28 shows a geometric pattern of apertures 90 that includes skewed shaped apertures 76 and the tiles 92 configured therebetween.

FIG. 29 shows a geometric pattern of apertures 90 including cross-shaped apertures 78 between skewed shaped apertures 76.

Figure 30:
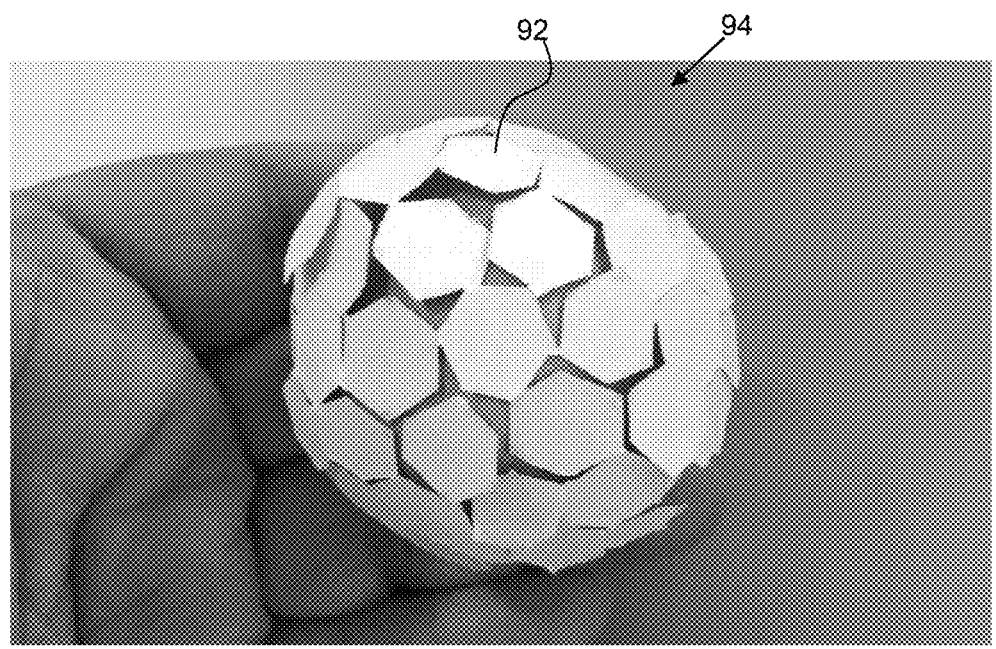
FIG. 30 shows an exemplary compliant biological scaffold material configured around a sphere.
Figure 31:
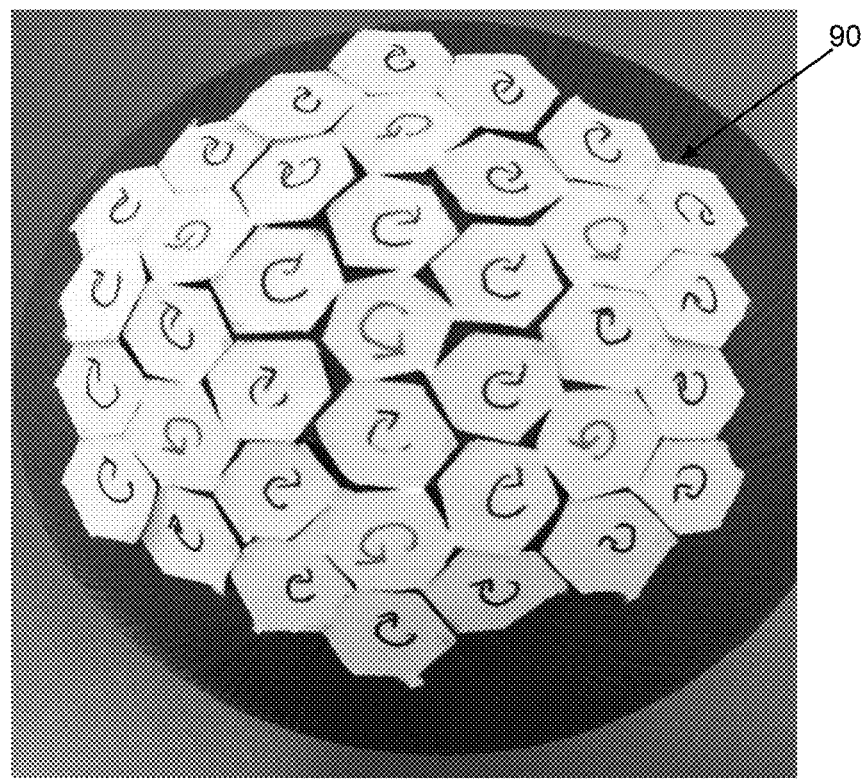
FIG. 31 show the rotational direction of the spherical compliant biological scaffold material with some tiles co-rotating and some counter rotating.

As shown in FIG. 30, and exemplary compliant biological scaffold 10 can comprise a plurality of apertures configured with the antinodes proximal to a node to produce geometric shapes or tiles 92. The compliant biological scaffold is expanded and forms a compliant spherical shape. FIG. 31 show the rotational direction of the spherical compliant biological scaffold material with some tiles co-rotating and some counter rotating.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A compliant biological scaffold comprising:
   a) a plurality of elongated apertures in said compliant biological scaffold that forms a geometric pattern, each of said plurality of elongated apertures comprising:
      i) a pair of nodes; and
      ii) a pair of antinodes;
   wherein the pair of nodes are centrally located along the elongated aperture with a first node on a first side of the elongated aperture and a second node on a second side of the elongated aperture; and
   wherein a first antinode is configured on a first antinode end of the elongated aperture and a second antinode is configured on a second antinode end of the elongated aperture;
   b) a plurality of geometric shapes having a bounded perimeter formed by said plurality of elongated apertures;
      wherein upon biaxially expanding the compliant biological scaffold material, the first and second nodes separate from each other and wherein a distance between the antinodes contracts to form an arrangement of tessellated apertures in the graft material;
      wherein the plurality of elongated apertures forms said geometric pattern with a substantial portion of elongated apertures configured with the antinodes proximal to one of said pair of nodes of a separate elongated aperture; wherein the antinodes are closer to said one of said pair of nodes than to any other antinode; and
      wherein the plurality of elongated apertures comprises expanded elongated apertures.

2. The compliant biological scaffold of claim 1, wherein the plurality of elongated apertures comprised of linear elongated apertures.

3. The compliant biological scaffold of claim 1, wherein the plurality of elongated apertures consists of linear elongated apertures.

4. The compliant biological scaffold of claim 1, wherein the plurality of elongated apertures consists of expanded elongated apertures.

5. The compliant biological scaffold of claim 1, wherein a substantial portion of the elongated apertures are arranged orthogonally to each other, wherein a first elongated aperture is orthogonal to a second elongated aperture configured on a first antinode end of said first elongated aperture.

6. The compliant biological scaffold of claim 5, wherein the first antinode end of the first elongated aperture is proximal to a first node of the second elongated aperture.

7. The compliant biological scaffold of claim 5, wherein a length axis of the first elongated aperture extends through a first node of the second elongated aperture.

8. The compliant biological scaffold of claim 5, wherein a length axis of the first elongated aperture extends centrally through the second elongated aperture.

9. The compliant biological scaffold of claim 5, wherein a substantial portion of the elongated apertures are arranged in a I-configuration, wherein a first elongated aperture is substantially orthogonal to a second elongated aperture configured on the first antinode end of said first elongated aperture and wherein said first elongated aperture is substantially orthogonal to a third elongated aperture configured on the second antinode end of said first elongated aperture.

10. The compliant biological scaffold of claim 1, comprising two pairs of nodes configured between antinodes along said elongated aperture.

11. The compliant biological scaffold of claim 1, wherein the geometric pattern of elongated apertures comprises T-shaped apertures.

12. The compliant biological scaffold of claim 1, wherein the geometric pattern of elongated apertures comprises Y-shaped apertures.

13. The compliant biological scaffold of claim 1, wherein the geometric pattern of elongated apertures comprises skewed-shaped apertures.

14. The compliant biological scaffold of claim 1, wherein the geometric pattern of elongated apertures comprises cross-shaped apertures.

15. The compliant biological scaffold of claim 1, wherein the geometric shape has a plurality of corners and wherein each of said plurality of corners are bound by a node of separate elongated apertures.

16. The compliant biological scaffold of claim 1, wherein the geometric shape is a rectangle and wherein the corners of the rectangle are bound by a node of four separate elongated apertures.

17. The compliant biological scaffold of claim 1, wherein the geometric shape is a triangle and wherein the corners of the rectangle are bound by a node of three separate elongated apertures.

18. The compliant biological scaffold of claim 17, wherein the plurality of elongated apertures comprises expanded elongated apertures.

19. The compliant biological scaffold of claim 1, wherein the geometric shape consists essentially of a single geometric shape.

20. The compliant biological scaffold of claim 1, wherein the geometric pattern comprises two or more geometric shapes.

21. The compliant biological scaffold of claim 1, wherein the compliant biological scaffold comprises a biological material derived from a living organism.

22. The compliant biological scaffold of claim 21, wherein the biological material comprises epidermis.

23. The compliant biological scaffold of claim 21, wherein the biological material comprises bone.

24. The compliant biological scaffold of claim 1, wherein each of the elongated apertures has a length of 1 mm or less.

25. The compliant biological scaffold of claim 1, comprising a first portion with the plurality of elongated apertures being expanded elongated apertures and a second portion wherein the plurality of elongated apertures are not expanded elongated apertures portion whereby the first portion of the compliant biological scaffold is configured contraction and whereby the second portion of the compliant biological scaffold is configured for expansion.

26. The compliant biological scaffold of claim 1, wherein the compliant biological scaffold comprises a polymeric material.

27. A compliant biological scaffold comprising:
a) a plurality of elongated apertures in said compliant biological scaffold that forms a geometric pattern, each of said plurality of elongated apertures comprising:
   i) a pair of nodes; and
   ii) a pair of antinodes;
   wherein the pair of nodes are centrally located along the elongated aperture with a first node on a first side of the elongated aperture and a second node on a second side of the elongated aperture; and
   wherein a first antinode is configured on a first antinode end of the elongated aperture and a second antinode is configured on a second antinode end of the elongated aperture;
b) a plurality of geometric shapes having a bounded perimeter formed by said plurality of elongated apertures;
   wherein upon biaxially expanding the compliant biological scaffold material, the first and second nodes separate from each other and wherein a distance between the antinodes contracts to form an arrangement of tessellated apertures in the graft material;
   wherein the plurality of elongated apertures forms said geometric pattern with a substantial portion of elongated apertures configured with the antinodes proximal to one of said pair of nodes of a separate elongated aperture; wherein the antinodes are closer to said one of said pair of nodes than to any other antinode; and
   comprising three antinodes configured on antinode ends of separate extensions of an elongated aperture, wherein each of the extensions of the elongated apertures extend from the pair of nodes to a separate antinode.

28. The compliant biological scaffold of claim 27, wherein the separate extensions are configured substantially equidistant circumferentially from each other.

29. A compliant biological scaffold comprising:
a) a plurality of elongated apertures in said compliant biological scaffold that forms a geometric pattern, each of said plurality of elongated apertures comprising:
   i) a pair of nodes; and
   ii) a pair of antinodes;
   wherein the pair of nodes are centrally located along the elongated aperture with a first node on a first side of the elongated aperture and a second node on a second side of the elongated aperture; and
   wherein a first antinode is configured on a first antinode end of the elongated aperture and a second antinode is configured on a second antinode end of the elongated aperture;
b) a plurality of geometric shapes having a bounded perimeter formed by said plurality of elongated apertures;
   wherein upon biaxially expanding the compliant biological scaffold material, the first and second nodes separate from each other and wherein a distance between the antinodes contracts to form an arrangement of tessellated apertures in the graft material;
   wherein the plurality of elongated apertures forms said geometric pattern with a substantial portion of elongated apertures configured with the antinodes proximal to one of said pair of nodes of a separate elongated aperture; wherein the antinodes are closer to said one of said pair of nodes than to any other antinode; and
   wherein the compliant biological scaffold comprises a biological material that is metal or a metal alloy.

30. A method of producing a compliant biological scaffold comprising:
a) providing a biological material;
b) forming a geometric pattern of a plurality of elongated apertures in said biological material to form said compliant biological scaffold, each of said plurality of elongated apertures comprising:
   i) a pair of nodes; and
   ii) a pair of antinodes;
   wherein the pair of nodes are centrally located along the elongated aperture with a first node on a first side of the elongated aperture and a second node on a second side of the elongated aperture; and
   wherein a first antinode is configured on a first antinode end of the elongated aperture and a second antinode is configured on a second antinode end of the elongated aperture;
   wherein the plurality of elongated apertures forms a plurality of geometric shapes having a bounded perimeter;
c) biaxially expanding the compliant biological scaffold material, wherein upon biaxially expanding the compliant biological scaffold the first and second nodes separate from each other and wherein a distance between the antinodes contracts to form an arrangement of tessellated apertures in the biological material;
   wherein the plurality of elongated apertures forms a geometric pattern with a substantial portion of elongated apertures configured with the antinodes proximal to one of said pair of nodes of a separate elongated aperture; wherein the antinodes are closer to said one of said pair of nodes than to any other antinode;
   wherein the compliant biological scaffold is formed in vivo wherein the biological material is an in vivo tissue and wherein the geometric pattern of the plurality of elongated apertures are formed in vivo.

31. The method of claim 30, comprising cutting into a patient to expose the said biological material and then forming said plurality of elongated apertures in said biological material to form said compliant biological scaffold in vivo.

32. The method of producing a compliant biological scaffold of claim 31, wherein the biological scaffold is bone and further comprising:
d) forming a geometric pattern of elongated apertures in said bone;
e) allowing said bone to reconfigure into a new shape.

33. The method of claim 32, wherein said bone has a bone fracture;
   wherein forming said geometric pattern of elongated apertures is said bone is done proximal to the bone fracture; and wherein the method further comprises allowing said bone to heal and expand across the fracture.

34. The method of claim 32, wherein the geometric pattern of elongated apertures comprises expanded elongated apertures.

35. A method of producing a compliant biological scaffold comprising:
a) providing a biological material;
b) forming a geometric pattern of a plurality of elongated apertures in said biological material to form said compliant biological scaffold, each of said plurality of elongated apertures comprising:

i) a pair of nodes; and
  ii) a pair of antinodes;
 wherein the pair of nodes are centrally located along the elongated aperture with a first node on a first side of the elongated aperture and a second node on a second side of the elongated aperture; and
 wherein a first antinode is configured on a first antinode end of the elongated aperture and a second antinode is configured on a second antinode end of the elongated aperture;
 wherein the plurality of elongated apertures forms a plurality of geometric shapes having a bounded perimeter;
c) biaxially expanding the compliant biological scaffold material, wherein upon biaxially expanding the compliant biological scaffold the first and second nodes separate from each other and wherein a distance between the antinodes contracts to form an arrangement of tessellated apertures in the graft-biological material;
  wherein the plurality of elongated apertures forms a geometric pattern with a substantial portion of elongated apertures configured with the antinodes proximal to one of said pair of nodes of a separate elongated aperture; wherein the antinodes are closer to said one of said pair of node than to any other antinode;
  wherein the plurality of elongated apertures comprises expanded elongated apertures.

36. The method of claim 35, wherein the plurality of elongated apertures consists of expanded elongated apertures.

37. The method of claim 35 further comprising:
  d) providing a cutting template having a cutting pattern for the geometric pattern of a plurality of elongated apertures thereon; and
  e) placing said cutting template over the biological material to guide forming said geometric pattern of a plurality of elongated apertures in said biological material.

38. The compliant biological scaffold of claim 35, wherein the biological material comprises skin and wherein the compliant biological scaffold is formed in vivo wherein the biological material is an in vivo tissue and wherein the geometric pattern of the plurality of elongated apertures are formed in vivo.

39. The compliant biological scaffold of claim 38, wherein the length of the apertures is microscopic having a length less than a millimeter.

\* \* \* \* \*